(12) United States Patent
Schmitz et al.

(10) Patent No.: US 9,646,812 B2
(45) Date of Patent: May 9, 2017

(54) MALDI SAMPLE PREPARATION METHODS AND TARGETS

(76) Inventors: Oliver J. Schmitz, Wuppertal (DE); Volker Wulf, Langenfeld (DE); Lukas Hyzak, Wuppertal (DE); Michaela Wirtz, Wuppertal (DE); David Melchior, Bergisch Gladbach (DE); Hans Willi Kling, Wuppertal (DE); Siegmar Gäb, Wuppertal (DE); Ursula Gäb, legal representative, Cologne (DE)

( * ) Notice: Subject to any disclaimer, the term of this patent is extended or adjusted under 35 U.S.C. 154(b) by 0 days.

(21) Appl. No.: 14/234,772

(22) PCT Filed: Jul. 25, 2012

(86) PCT No.: PCT/GB2012/051782
§ 371 (c)(1),
(2), (4) Date: Jan. 20, 2015

(87) PCT Pub. No.: WO2013/014447
PCT Pub. Date: Jan. 31, 2013

(65) Prior Publication Data
US 2015/0162176 A1    Jun. 11, 2015

(30) Foreign Application Priority Data
Jul. 26, 2011 (GB) .................................. 1112892.3

(51) Int. Cl.
*H01J 49/00* (2006.01)
*H01J 49/04* (2006.01)
(Continued)

(52) U.S. Cl.
CPC ............ *H01J 49/0031* (2013.01); *G01N 1/38* (2013.01); *H01J 49/0036* (2013.01);
(Continued)

(58) Field of Classification Search
USPC .......................................................... 250/282
See application file for complete search history.

(56) References Cited

U.S. PATENT DOCUMENTS 5,770,860 A * 6/1998 Franzen .............. H01J 49/0418
250/288
5,777,324 A * 7/1998 Hillenkamp .......... H01J 49/164
250/288

(Continued)

FOREIGN PATENT DOCUMENTS

JP    2007-309860 A    11/2007
WO    WO 01/61054 A2    2/2001
(Continued)

OTHER PUBLICATIONS

International Search Report and Written Opinion dated Dec. 13, 2012 corresponding to International Patent Application No. PCT/GB2012/051782.

(Continued)

*Primary Examiner* — Phillip A Johnston
(74) *Attorney, Agent, or Firm* — Sughrue Mion, PLLC

(57) ABSTRACT

The present invention is concerned with a method of preparing a MALDI sample, the method comprising the steps of: (a) mixing a solid sample precursor comprising sample and matrix to form a solid sample mixture; (b) applying the solid sample mixture to a sample cavity of a MALDI target; and (c) compressing the solid sample mixture in the sample cavity so as to form a MALDI sample surface for laser desorption. The present invention also provides a MALDI target comprising a sample cavity for receiving a MALDI sample, the sample cavity having (a) a desorption end portion comprising an aperture, such that a portion of the MALDI sample exposed at the aperture is in use subjected to laser desorption; and wherein the sample cavity also has (b) a compression end portion adapted to permit compres- (Continued)

sion of a solid sample mixture towards the desorption end portion in the sample cavity by applying a compression force to the solid sample mixture via the compression end portion.

14 Claims, 8 Drawing Sheets

(51) Int. Cl.
  *G01N 1/38*     (2006.01)
  *H01J 49/16*     (2006.01)
(52) U.S. Cl.
  CPC ...... *H01J 49/0418* (2013.01); *H01J 49/0459* (2013.01); *H01J 49/164* (2013.01)

(56) References Cited

U.S. PATENT DOCUMENTS

| | | | |
|---|---|---|---|
| 6,844,545 B1 | 1/2005 | Hutchins et al. | |
| 7,283,228 B2* | 10/2007 | Zhang | B82Y 30/00 356/244 |
| 8,174,691 B1* | 5/2012 | Horton | G01N 1/02 356/244 |
| 2002/0151040 A1 | 10/2002 | O'Keefe et al. | |
| 2003/0010908 A1 | 1/2003 | Clark et al. | |
| 2006/0252047 A1 | 11/2006 | Ekstrom et al. | |

FOREIGN PATENT DOCUMENTS

| | | |
|---|---|---|
| WO | WO 03/081205 A2 | 10/2003 |
| WO | WO 2005/008244 A1 | 1/2005 |
| WO | WO 20071022026 A2 | 2/2007 |

OTHER PUBLICATIONS

S. Trimpin et al., "Solvent-Free MALDI-MS: Developmental Improvements in the Reliability and the Potential of MALDI in the Analysis of Synthetic Polymers and Giant Organic Molecules," American Society for Mass Spectrometry, Jan. 16, 2006, vol. 17, pp. 661-671.

S. Trimpin et al., "New Aspects in Matrix-Assisted Laser Desorption/Ionization Time-of-Flight Mass Spectrometry: a Universal Solvent-Free Sample Preparation," Rapid Communications in Mass Spectrometry, Aug. 15, 2001, pp. 1364-1373.

Laurence Przybilla et al., "MALDI-TOF Mass Spectrometry of Insoluble Giant Polycyclic Aromatic Hydrocarbons by a New Method of Sample Preparation," Analytical Chemistry, vol. 72, No. 19, Oct. 1, 2000, pp. 4591-4597.

Anna Cristadoro et al.., "Quantitative Analyses of Fullerene and Polycyclic Aromatic Hydrocarbon Mixtures via Solvent-Free Matrix-Assisted Laser Desorption/Ionization Mass Spectrometry," Rapid Communications in Mass Spectrometry, vol. 22, 2008, pp. 2463-2470.

Scott D. Hanton et al., "Extending the Solvent-Free MALDI Sample Preparation Method," American Society of Mass Spectrometry, vol. 16, No. 1, 2005, pp. 90-93.

Lukas Hyzak et al., "Quantitative Matrix-Assisted Laser Desorption Ionization-Time-of-Flight Mass Spectrometry Analysis of Synthetic Polymers and Peptides," Analytical Chemistry, vol. 83, 2011, pp. 9467-9471.

Wei Chao Chang et al., "Matrix Assisted Laser Desoption/Ionization (MALDI) Mechanism Revisited," Analytica Chimica Acta 582, 2007, pp. 1-9.

Steffen M. Weidner et al., "Imaging Mass Spectrometry for Examining Localization of Polymeric Composition in Matrix-Assisted Laser Desorption/Ionization Samples," Rapid Communications in Mass Spectrometry, vol. 23, 2009, pp. 653-660.

Nahid Amini et al., "SALDI-MS Signal Enhancement Using Oxidized Graphitized Carbon Black Nanoparticles," American Society for Mass Spectrometry, vol. 20, 2009, pp. 1207-1213.

Emilia Szajli et al., "Investigating the Quantitative Nature of MALDI-TOF MS*," Molecular & Cellular Proteomics, 2008, 7, pp. 2410-2418. Supplementary Material (49 pages).

Martin Buknall et al., "Practical Quantitative Biomedical Applications of MALDI-TOF Mass Spectrometry," American Society for Mass Spectrometry, 2002, 13, pp. 1015-1027.

Wenyan Yan et al., "Quantitative Analysis of Technical Polymer Mixtures by Matrix Assisted Laser Desorption/Ionization Time of Flight Mass Spectrometry," American Society for Mass Spectrometry, 2002, 13, pp. 914-920.

* cited by examiner

MALDI SAMPLE PREPARATION METHODS AND TARGETS

TECHNICAL FIELD OF THE INVENTION

The present invention relates to a MALDI target, a method of preparing a MALDI sample and a method of quantitative analysis of results obtained by mass spectrometry using the MALDI target or the method of preparing a MALDI sample.

BACKGROUND

Ionization of non-volatile and thermally unstable biomolecules, as well as many synthetic polymers, is possible by the use of soft ionization techniques like electrospray ionization (ESI) and matrix-assisted laser desorption/ionization (MALDI). MALDI in particular is a useful technique and is able to determine the molecular weight of polar to relatively non-polar analytes in a mass range of 300 to over 1,000,000 Da without fragmentation.[1] In contrast to ESI, MALDI produces ions with only one charge, so that the interpretation is facilitated. In addition, ESI ionizes only polar to moderately polar substances, and discrimination effects are frequently observed with compounds of high molecular weight.

The result of a MALDI analysis is highly dependent on the sample preparation. The dried droplet (DD) technique (also known as solvent evaporation technique) is the most commonly used method because it is very easy to carry out.[1] For this purpose, the substances to be analysed and matrix are applied to the target dissolved in a suitable solvent. The solvent then evaporates to leave solid matrix and analyte, which can then be desorbed by action of the MALDI laser. Whilst the DD technique permits rapid sample preparation and is amenable to scaling up (using "target printing" techniques) to form large numbers of samples simultaneously, it has significant drawbacks in terms of sample quality and reproducibility. In particular, solvent evaporation leads to inhomogeneous crystallization, so that chromatographic effects result and lead to a concentration distribution of the analyte on the target.[2] in the case of the analysis of a synthetic polymer, it can even result in a spatial distribution of oligomers within a single sample.[2] Thus under solvent-based conditions reproducible results are difficult to obtain.[2] This prevents widespread industrial use of this otherwise very powerful mass spectrometric method.

Some attempts have been made to address these drawbacks. In particular, it has been suggested that improved homogeneity can be achieved using solvent-free sample preparation techniques. It has been proposed that solvent can be excluded by grinding the solid sample and spreading the resulting powder on a sample plate.[7-10]

A solvent-free method where the solid sample powder is highly compressed into a pellet has also been suggested,[8-10] the compressed pellet is attached to the sample plate by double sided conductive tape.[8] However, the high density of the compressed pellet has been found by the author to hamper desorption.[8] The same authors found that direct powder application shows better resolution and sensitivity than the pressed pellet application.[8-10] It has been suggested that the method of transferring the sample to the MALDI target plate influences sensitivity and mass resolution, saying that employing loose powder transfer, rather than transferring the compressed pellet, improves sensitivity and gives higher mass resolution.[16]

SUMMARY OF THE INVENTION

The present inventors have noted that attempts at solvent-free MALDI sample preparation have not been entirely successful. The variation coefficient of the results obtained by MALDI mass spectrometry of solvent-free samples of the prior art have been calculated by the present inventors are as low as 0.09-0.23 when chemically related compounds are used as internal standards.[7] These results were obtained for model systems; therefore the variation coefficient for results obtained for real samples is likely to be much higher for the methods of the prior art.

Additionally the present inventors have noted that despite the above referenced efforts to design a solvent-free approach in the vast majority of cases the prior art uses solvent-based approaches for quantification. Whilst these techniques allow quantification with a relative standard deviation of about 10% with stable-isotope-labeled internal standards,[3-5] isotope-labeled standards are in most cases not available, so that structural analogs have to be used as internal standards. As a result, the variation coefficient increase dramatically for these methods.[5-6]

The provision of routine satisfactory quantitative analysis using MALDI has not yet been achieved in the art. The present inventors have addressed this problem as discussed herein.

As a result of their studies, the present inventors have found that the reproducibility of results obtained by MALDI mass spectrometry can be improved by addressing some or all of the following technical challenges: improving the scruple surface homogeneity, improving the sample surface flatness and improving the accuracy and control of the distance between detector and sample surface.

The present invention seeks to improve the reproducibility of results obtained by mass spectrometry. In particular, embodiments of the present invention seek to allow quantitative analysis of samples such as synthetic polymers and peptides with MALDI mass spectrometry by producing reproducible results (results with low variation coefficient) with good mass resolution.

A first proposal is that a method of preparing a MALDI sample includes the steps of mixing a solid sample precursor and compressing the resulting solid sample mixture within a sample cavity of a MALDI target, such that a flat and homogeneous MALDI sample surface can be formed in situ.

A second proposal is that a MALDI target is provided with a sample cavity having a compression end and a desorption end, such that a solid sample mixture may be compressed within the sample cavity of the MALDI target to form a flat MALDI sample surface at the desorption end of the sample cavity.

A third proposal is that a method of quantitative analysis of a sample includes forming a flat and homogeneous MALDI sample surface in situ in a MALDI target, such that reproducible results are obtained by analysis of the MALDI sample surface in a mass spectrometer, the reproducible results then being quantitatively analysed with reference to a standard.

Each of these proposals is discussed in turn.

In respect of the first proposal, the problem of providing a sample from which reproducible results can be obtained by MALDI mass spectrometry is addressed by providing a method in which the sample is mixed and then transferred to a sample cavity of a MALDI target within which the sample is then compressed.

In a first aspect the present invention provides a method of preparing a MALDI sample, the method comprising the steps of:

(a) mixing a solid sample precursor comprising sample and matrix to form a solid sample mixture;
(b) applying the solid sample mixture to a sample cavity of a MALDI target; and
(c) compressing the solid sample mixture in the sample cavity so as to form a MALDI sample surface for laser desorption.

The present inventors have found that advantages arising from the use of this method may include: ease of use, reproducibility of results, minimal loss of sample, user-independent results, suitability for large scale and/or industrial use as well as minimal training requirements for the user. Other advantages are discussed herein.

As a result of this method the MALDI sample formed advantageously has a substantially flat surface. Furthermore, experiments conducted by the present inventors show that even distribution of sample throughout the matrix of the MALDI sample can be achieved using this method.

The advantages associated with the use of this method enable reproducible results to be obtained by MALDI mass spectrometry. Reproducible results are results with a low variation coefficient. Preferably the variation coefficient is no more than 0.095, more preferably no more than 0.090, more preferably no more than 0.080, more preferably no more than 0.070, more preferably no more than 0.060 and most preferably no more than 0.050. In embodiments, a variation coefficient of about 0.040 or less is achieved. These impressive values for variation coefficient permit quantitative analysis of an analyte.

Mixing

The mixing step ensures adequate mixing of matrix and sample such that the sample is distributed evenly, i.e. homogeneously, throughout the matrix. Mixing is necessary to ensure that the MALDI sample has substantially the same composition at all points on the desorption surface. A homogeneous desorption surface allows the matrix and sample to be desorbed at the same time from the MALDI sample surface in MALDI mass spectrometry, this ensures that the gas plume includes a mixture of sample and matrix. This is in contrast to the DD technique of the prior art where solvent evaporation leads to inhomogeneous crystallization and therefore a concentration distribution of the sample on the MALDI sample surface. A further advantage of the present invention is that some variation in the location of the MALDI laser impact site on the MALDI sample surface can be tolerated because of the homogeneous distribution of sample.

The solid sample precursor may be mixed using any suitable means, manual or automated. A mortar with a pestle or a ball mill can be used. Optionally the ball mill may be cooled.

In embodiments, the matrix comprises two or more matrix components. Suitable matrix components are discussed herein, for example, 2,5-dihydroxybenzoic acid, α-cyano-4-hydroxycinnamic acid (CHCA) and sinapic acid. In other embodiments, only a single matrix component is used.

Preferably mixing step (a) comprises (i) mixing the matrix components and (ii) adding the sample to the mixed matrix components. Suitably mixing step (a) comprises (iii) mixing the sample and the mixed matrix components.

Suitably mixing step (a) comprises (iv) grinding the sample and/or matrix and/or solid sample mixture.

Grinding can reduce particle size and/or improve particle size homogeneity.

Preferably the solid sample mixture has (for example, as a result of grinding) a small sample particle size, suitably a small average particle size. Suitably the sample particle size, suitably the average particle size, is less than about 20 µm, more preferably less than about 15 µm, and most preferably about 10 µm or less. Sample particle size, suitably average particle size, can be measured by conventional means, for example from SEM photographs (e.g. see FIG. 4d).

Typically the sample will be analysed so as to identify, and preferably quantify, a particular substance, i.e. an analyte. For example, the analyte can be a particular polymer or peptide/protein. Accordingly, in embodiments, the sample comprises an analyte, optionally more than one analyte.

Suitably the analyte is any analyte with a mass greater than about 300 Da.

Preferably the analyte can be ionized.

Suitably the analyte is a polymer or peptide (e.g. a protein).

Preferably the solid sample precursor includes a standard. Suitably the standard is chemically similar to a particular substance in the sample that is to be analysed (i.e. an analyte). For example, suitably the standard belongs to the same chemical class of compounds as the analyte. In particular, if the analyte is a polymer the standard is preferably also a polymer; if the analyte is a peptide the standard is preferably also a peptide; and if the analyte is a protein the standard is preferably also a protein. An advantage of the present invention is that results may be obtained using a standard that is merely similar to the analyte, without the use of stable isotope labeled internal standards, which as noted above are not always available.

Suitably the solid sample precursor does not include an isotope labeled internal standard.

Suitably no isotope labeled internal standard is used in the method according to the first aspect.

Compressing

Compressing the solid sample mixture within the sample cavity of a MALDI target, i.e. in situ, allows a substantially flat MALDI sample surface, having a homogeneous distribution of sample and matrix, to be formed. In addition, the compressed MALDI sample has desirable bulk properties. The substantially flat and homogeneous MALDI sample surface allows reproducible results to be obtained by mass spectrometry, that is, results with a low variation coefficient as defined herein.

Preferably the MALDI sample surface formed has a maximum height variation (i.e. distance between lowest and highest points on the surface) of less than 50 µm, preferably 20 µm or less, more preferably 10 to 20 µm, more preferably 10 µm or less, more preferably 5 µm or less.

Preferably the particles of the solid sample mixture show good packing on compression. Good packing improves the robustness of the sample by substantially eliminating the occurrence of voids. Thus, in embodiments the compressed MALDI sample is substantially free of voids. Preferably the compressed MALDI sample has a robust structure so that the structure is not altered under the vacuum conditions of MALDI.

The maximum height variation of the MALDI sample surface may be measured by any method of measuring surface topography known to the skilled person. Suitably the maximum height variation may be measured by non-contact methods, for example using optical microscopy, or scanning electron microscopy. Alternatively, the height variation can be measured by contact methods such as with a Surface Profilometer or an Atomic Force Microscope (AFM).

The mass resolution of a MALDI instrument can be dependent on the sample surface roughness the greater the sample height variation, the poorer the mass resolution. Therefore, alternatively or additionally, the maximum height variation may be determined from the mass resolution.

Preferably the MALDI sample surface formed in step (c) is substantially level with the front surface of MALDI target (i.e. the surface of the MALDI target which in use faces the laser beam, typically this is the desorption end portion of the MALDI target). This allows a substantially flat and homogeneous MALDI sample surface with a defined distance between the MALDI sample surface and the detector to be obtained. In mass spectrometry it is conventional to identify ions arriving at the detector based on their travel time from the MALDI sample to the detector. To determine this precisely the distance between the MALDI sample surface and the detector must be known. Therefore the MALDI sample surface being substantially level with the front surface of the MALDI target further improves the precision of the determination of mass by mass spectrometry.

The height variation between the MALDI sample surface and the front surface of the MALDI target (i.e. the distance between the front surface of the MALDI target and the MALDI sample surface) may be determined by any method suitable for determining the maximum height variation of the sample, for example optical measurements.

Preferably the height variation between the MALDI sample surface and the front surface of the MALDI target is less than about 50 µm, preferably 20 µm or less, more preferably 10 to 20 µm, more preferably 10 µm or less, more preferably 5 µm or less.

Preferably the MALDI sample surface formed in step (c) is formed by compressing the solid sample mixture against a surface forming means. The surface forming means may be removed after compression of the MALDI sample.

The surface forming means may be any surface suitable to compress a sample against. Preferably the surface forming means is flat and rigid. Preferably the surface forming means is attachable to the MALDI target. The surface forming means can be a cover that is placed over the sample cavity. Optionally the surface forming means is a glass slide. However, the surface forming means may be made of other materials e.g. metal.

Suitably the method includes, for example as part of step (c), e.g. step (c'), applying a sample support means to the back surface of the MALDI sample (i.e. the surface at the opposite end of the compressed sample to the MALDI sample surface and hence the surface of the MALDI sample which in use faces away from the laser beam and is therefore not ablated). The back surface of the MALDI sample typically corresponds to the compression end portion of the MALDI target sample cavity, i.e. the portion of the MALDI target cavity through which compression is facilitated, as discussed below. The sample support means serves to support the sample after it has been compressed. For example, it can assist in retaining the compressed sample in the cavity, e.g. during transport of the MALDI target. Supporting and retaining the compressed sample in this way not only permits more convenient movement of the MALDI target without loss of the sample, but it permits the MALDI target to be moved with the MALDI sample surface facing upwards. This can assist in preserving the integrity of the sample surface, which as discussed herein is important in achieving good reproducibility.

Preferably the sample support means can be applied to the compression end of the MALDI sample without inclusion of air between the MALDI sample and the sample support means. That is, suitably the sample support means abuts the back surface of the compressed sample.

In embodiments, the method includes, after compressing the sample mixture, step (c') applying a sample support means to the compression end (i.e. back surface) of the MALDI sample. Suitably the method includes transporting the MALDI target including the sample support means so that the compressed sample is retained in the sample cavity.

Suitably the sample support means may be any manual or automated feature that allows support of the MALDI sample within the sample cavity.

Preferably the sample support means is applied to the compression end of the MALDI sample before removal of the surface forming means from the front surface of the MALDI target.

Preferably the sample support means is attachable to the MALDI target. The sample support means can be a cover that is placed over the compression end portion of the sample cavity. Optionally the sample support means is tape e.g. adhesive tape. The sample support means may be made of other materials, e.g. metal or glass.

In embodiments, the sample support means is also the compression means.

Following the preparation of the MALDI sample surface, preferably the MALDI target comprising the MALDI sample surface is transferred to a MALDI mass spectrometer where the MALDI sample surface is ionized and the ions produced analysed by mass spectrometry. Suitably TOF mass spectrometry is used.

Following analysis of the MALDI sample surface by MALDI mass spectrometry, preferably the results are quantitatively analysed.

The homogenous and substantially flat MALDI sample surface with a defined distance to the detector allows quantitative analysis of the results such that a plurality of chemically related analytes can be quantified with only a single standard.

In respect of the second proposal, the problem of providing a MALDI target from which reproducible results can be obtained by MALDI mass spectrometry is addressed by providing a MALDI target with a sample cavity in which a solid sample mixture may be compressed towards the MALDI sample surface.

In a second aspect the present invention provides a MALDI target comprising a sample cavity for receiving a MALDI sample, the sample cavity having
 (a) a desorption end portion comprising an aperture, such that a portion of the MALDI sample exposed at the aperture is in use subjected to laser desorption;
 and wherein the sample cavity also has
 (b) a compression end portion adapted to permit compression of a solid sample mixture towards the desorption end portion in the sample cavity by applying a compression force to the solid sample mixture via the compression end portion.

Thus, in use, the solid sample mixture is compressed within the MALDI target plate towards the MALDI sample surface (i.e. towards the desorption portion of the MALDI sample which will be exposed at the desorption end portion in use). This permits the formation of a substantially flat MALDI sample surface. A substantially flat MALDI sample surface avows results with a low variation coefficient, for example as discussed above for the first aspect, to be obtained by mass spectrometry. The present inventors have found that the advantages associated with the first aspect also apply to the second aspect.

Preferably the MALDI sample surface formed has a maximum height variation of less than 50 µm, preferably 20 µm or less, more preferably 10 to 20 µm, more preferably 10 µm or less, more preferably 5 µm or less.

Preferably the substantially flat MALDI sample surface formed is substantially level with the desorption end portion of the MALDI target. The desorption end portion of the MALDI target is typically at least part of the front surface of the MALDI target (i.e. the surface of the MALDI target which in use faces the laser beam). Therefore, in use, the distance between the MALDI sample surface and the detector is substantially the same as that between the MALDI surface of the desorption end portion and the detector. Thus, in use, a defined distance between the substantially flat MALDI sample surface and the detector is achieved. This further improves the reproducibility of the results obtained by mass spectrometry.

Preferably the compression end portion comprises an aperture for receiving a compression means. Suitably compression means may be any mechanical feature, manual or automated, that allows compression of the solid sample mixture within the sample cavity. The compression means may be a plunger that is inserted through the aperture to compress the solid sample mixture within the sample cavity. The plunger may be a rounded pin.

Preferably the sample cavity is a through hole. In embodiments, compression of the solid sample mixture towards the desorption end portion is permitted by providing a surface forming means, suitably abutting or adjacent to the desorption end portion, against which the solid sample mixture can be compressed. Suitably the surface forming means is a cover that may be placed over the desorption end portion. Optionally the sample forming means is a glass slide. However, the sample forming means may be made of other materials e.g. metal.

In embodiments, a sample support means is provided to support/retain the MALDI sample within the sample cavity of the MALDI target. Suitably the sample support means is any supporting means that may be applied to the compression end of the MALDI sample to support the MALDI sample within the sample cavity. Optionally the sample support means is a tape, suitably an adhesive tape.

A MALDI target with a through hole provides the advantage that the target is straightforward to manufacture and use. It allows a substantially flat MALDI surface, preferably substantially level with the desorption end portion of the MIAMI target, of the compressed MALDI sample formed within the through hole to be provided.

Preferably the MALDI target comprises a plurality of sample cavities. Suitably the MALDI target comprises 6, 12, 24, 32, 48, 96, 384, or 1536 sample cavities. Suitably the layout or format of the sample cavities in the MALDI target correspond to the format of conventional microtitre plates. Suitably the sample cavities are arranged in a rectangular matrix, suitably a 2:3 rectangular matrix.

In other embodiments the MALDI target is or has the same format (e.g. same overall dimensions) as a microscope slide. For example, the overall dimensions are about 24 mm by about 76 mm.

In such "microscope" embodiments, the MALDI target may comprise the same number of cavities as discussed above, with 48 cavities particularly preferred. A rectangular matrix layout is preferred, with 3:1 matrix layout especially preferred (e.g. 12×4 cavities in the case of a 48 cavity "microscope" target).

Generally, the diameter of the sample cavity is in the range 0.5 mm to 4 mm, preferably about 1 mm to 3 mm. In embodiments, about 0.9 mm to about 1.9 mm is used, with about 0.9 mm and about 1.9 mm being preferred. In other embodiments about 2.8 mm is used.

Suitably the centre-to-centre spacing of the cavities is chosen to be similar to a microtitre plate format. For example, for a 96 "well" plate, the centre-to-centre spacing would be about 9 mm; for a 384 "well" plate, about 4.5 mm; and for a 1536 "well" plate, about 2.25 mm. Thus, the centre-to-centre spacing is typically in the range about 1 mm to about 15 mm, suitably about 2 mm to about 10 mm.

Generally, the thickness of the target is about 0.5 mm to about 10 mm, preferably in the range about 1 mm to about 5 mm, and more preferably about 2 mm to about 4 mm. In embodiments about 2 mm is used Generally, the target is made from metal, preferably stainless steel, or plastic. In the case of plastic/polymeric targets, the target can comprise a conductive coating and/or the plastic/polymer is conductive.

The cross-section of the sample cavity may take any shape, but most preferably the sample cavity has a circular cross-section.

In an embodiment the sample cavity is tapered, suitably from the compression end portion to the desorption end portion. This shape provides the advantage of requiring less sample than an untapered cavity.

In respect of the third proposal, the problem of quantitatively analysing results obtained from MALDI mass spectrometry is addressed by providing a flat and homogenous MALDI sample surface at a defined distance from the detector.

In a third aspect the present invention provides a method of quantitative analysis of a sample, the method comprising the steps of:
  (a) preparing a MALDI sample according to the first aspect, wherein the solid sample precursor includes a standard;
  (b) analysis of the MALDI sample in a mass spectrometer; and
  (c) quantitative analysis of the results obtained by mass spectrometry with reference to the standard.

The results obtained by mass spectrometry of a sample comprising a standard have good mass resolution and are reproducible (have a low variation coefficient). Therefore these results allow the quantitative analysis of synthetic polymers and peptides with a hitherto unknown accuracy for MALDI without the use of stable isotope labelled standards.

Suitably analysis of the MALDI sample step (b) comprises obtaining results from multiple samples, the multiple samples may be obtained from one target or multiple targets.

Suitably the method includes a calibration step. Preferably this calibration step includes obtaining results from a chemical standard. Preferably a single chemical standard is used.

Preferably quantitative analysis of the results step (c) includes calculating the amount of a particular chemical substance (i.e. an analyte), for example polymer, peptide or protein within the sample.

Naturally, in some cases, the method of the present invention may provide the result that a particular substance (i.e. analyte) is not present in a sample, which can be valuable information. Accordingly, in embodiments, the sample may not include analyte, therefore the results of the calculation in step (c) would be zero analyte present in the sample.

Not only do embodiments of the present invention allow the quantitative analysis of samples without the need for stable isotope labelled standards, they also allow a plurality of chemically related analytes to be quantified with a single standard.

Suitably the optional and preferred features of the other aspects, especially the first aspect, apply to this aspect.

In a fourth aspect the present invention provides a method of quantitative analysis of a sample, the method comprising the steps of:
  (a) mixing a solid sample precursor comprising sample, matrix and a standard to form a solid sample mixture;
  (b) applying the solid sample mixture to a sample cavity of the MALDI target of the second aspect;
  (c) compressing the solid sample in the sample cavity so as to form a MALDI sample surface for laser desorption;
  (d) analysis of the MALDI sample surface in a mass spectrometer;
  (e) quantitative analysis of the results obtained by mass spectrometry with reference to the standard.

The advantages associated with the third aspect also apply to this fourth aspect.

Suitably the optional and preferred features of the other aspects, especially the second and third aspect, apply to this aspect.

In a fifth aspect the present invention provides a method of manufacturing a MALDI target to produce a MALDI target according to the first aspect. Suitably the method comprises the step of forming a sample cavity. Preferably a plurality of sample cavities are formed.

In embodiments, the method step of forming a sample cavity comprises modifying a conventional MALDI target to produce a MALDI target according to the first aspect. Suitably modifying includes drilling through a wall of a well, or a plurality of wells, in a conventional MALDI target.

In a sixth aspect the present invention provides a MALDI target that is the product of the fourth aspect.

In a seventh aspect the present invention provides use of a MALDI target according to the first and/or sixth aspect in a method of quantitative analysis.

In an eighth aspect the present invention provides an apparatus for compressing a MALDI sample within a MALDI target.

The optional and preferred features of any one aspect can also apply to any of the other aspects. Furthermore, features disclosed in the context of a product (MALDI target) may also apply to a method as a corresponding method step, and vice versa.

BRIEF DESCRIPTION OF THE DRAWINGS

Embodiments of the invention and information illustrating the advantages and/or implementation of the invention are described below, by way of example only, with respect to the accompanying drawings in which.

DETAILED DESCRIPTION OF PREFERRED EMBODIMENTS AND EXAMPLES

MALDI Target

Figure 1:
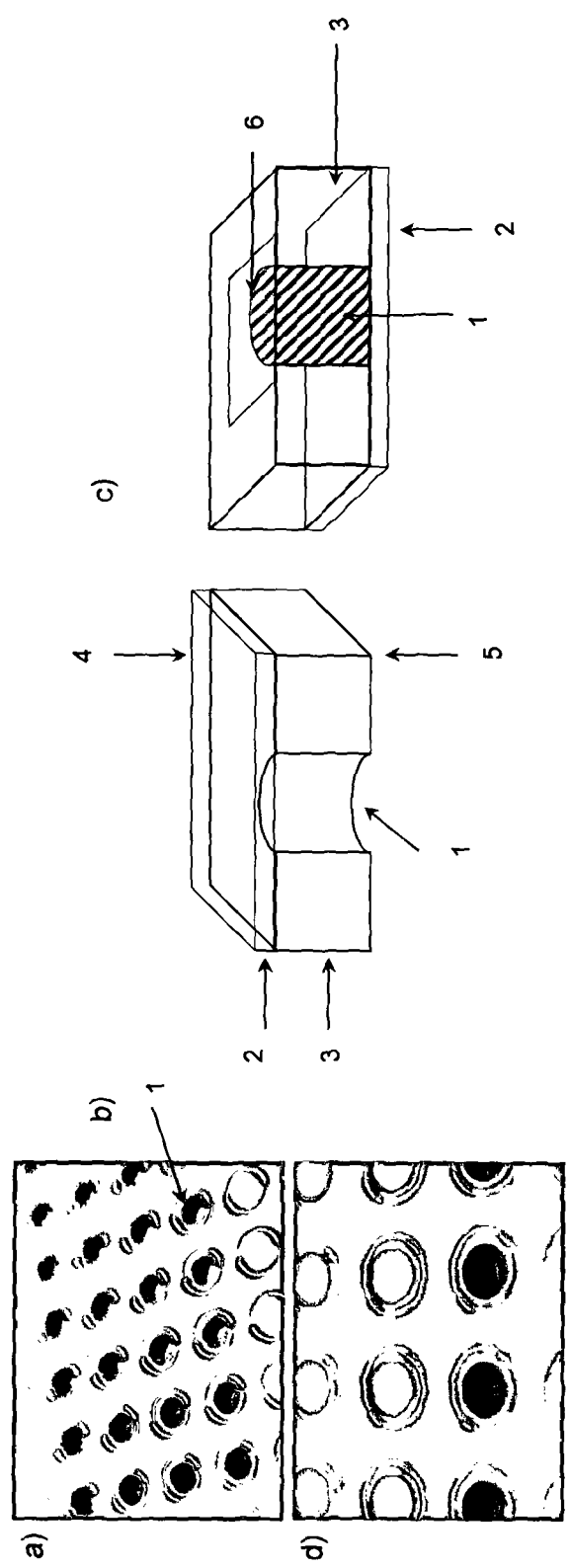
FIG. 1a is a photograph of a perforated stainless steel MALDI target.
FIG. 1b is a schematic diagram of a perforated stainless steel MALDI target.
FIG. 1c is a schematic diagram of a sample cavity filled with sample mixture.
FIG. 1d is a photograph of a sample cavity filled with sample mixture.

The MALDI target of the present invention allows quantitative analysis of synthetic polymers as well as peptides up to at least 2000 Da with MALDI-(TOF)MS. FIG. 1a shows an example of a MALDI target of the present invention. The 2-mm-thick stainless steel MALDI target from Shimadzu Europa GmbH containing 384 wells 1, which have been bored all the way through, the wells 1 have a diameter of 2.8 mm.

Method of Preparing a MALDI Sample

FIG. 1b and FIG. 1c illustrate an example of a method of preparing a MALDI sample. A microscope object slide 2, as the surface forming means, is temporarily fixed on the front of the target 3, and the target 3 is turned over. The solid sample mixture is placed in the sample cavity 1 and pressed against the object slide from the lower surface of the target 5 (compression end portion of target) with a metal pin as the compressing means. The sample cavity 1 is closed with adhesive tape 6 without any air inclusions, and the object slide 2 at the upper surface of the target 4 (desorption end portion of target) is removed. By this approach, a homogeneous, substantially flat surface with a defined distance between MALDI sample surface and the detector is obtained; this allows an isotopic resolution in the lower mass range up to 1800 Da.

Figure 2:
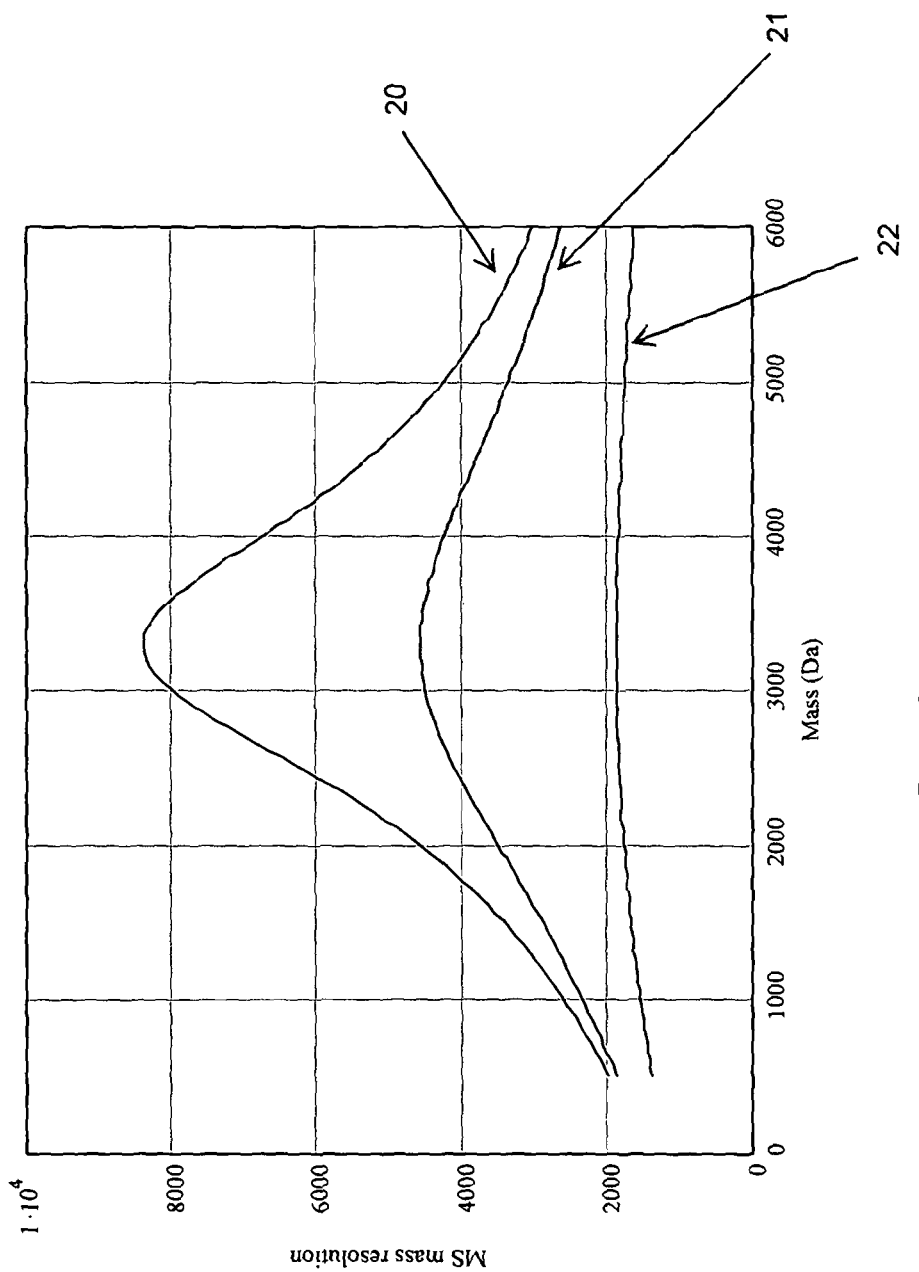
FIG. 2 shows the graphical plot of mass resolution for maximum height variations of 10 µm (20), 20 µm (21) and 50 µm (22) achieved against variation in height for a typical reflectron mode instrument.

FIG. 2 shows the effect of variation in sample height from theoretical simulations. The improvement in mass resolution can be seen as surface height variation is reduced from 50 µm (22) to 20 µm (21) and then 10 µm (20), showing the huge improvement in mass resolution achieved as the surface height variation decreases.

The present inventors have found that, when using a 100 µm laser, a sample surface height variation of more than 20 µm leads to low resolution. Resolution can be improved by decreasing the sample surface height variation to 10 µm or more preferably 5 µm. In order to obtain a mass resolution approaching 10,000 the present inventors have found that the surface height variation must be less than 10 µm.

Example 1

For the sample preparation a premix, consisting of all matrix components, is homogenized in a mortar with a pestle. A solvent-based analyte addition is used to add the sample and the internal standard to a premix aliquot (the small amounts of solvent evaporate within a short time) and afterwards the mixture is homogenized with a pestle. Alternatively, this can be done with a ball mill that can be cooled.

With a solid sample mixture prepared in this way, consisting of 20 mg sample material (including matrix), four sample cavities are filled to allow a fourfold determination. All analyses were performed on the AXIMA Performance™ MALDI-instrument (Shimadzu). The instrument was equipped with a pulsed nitrogen laser ($\lambda$=337 nm) delivering 3 ns laser pulses and a nominal energy of 100 µJ/laser shot. The premix consisted of 5.4 mg 2,5-dihydroxybenzoic acid (DHB), 5.4 mg aminopyrazine (AP) and 10.8 mg NaCl, with 0.19 mg raffinose. Around laser raster with 241 profiles and 2 laser shots per profile were used.

Figure 3:
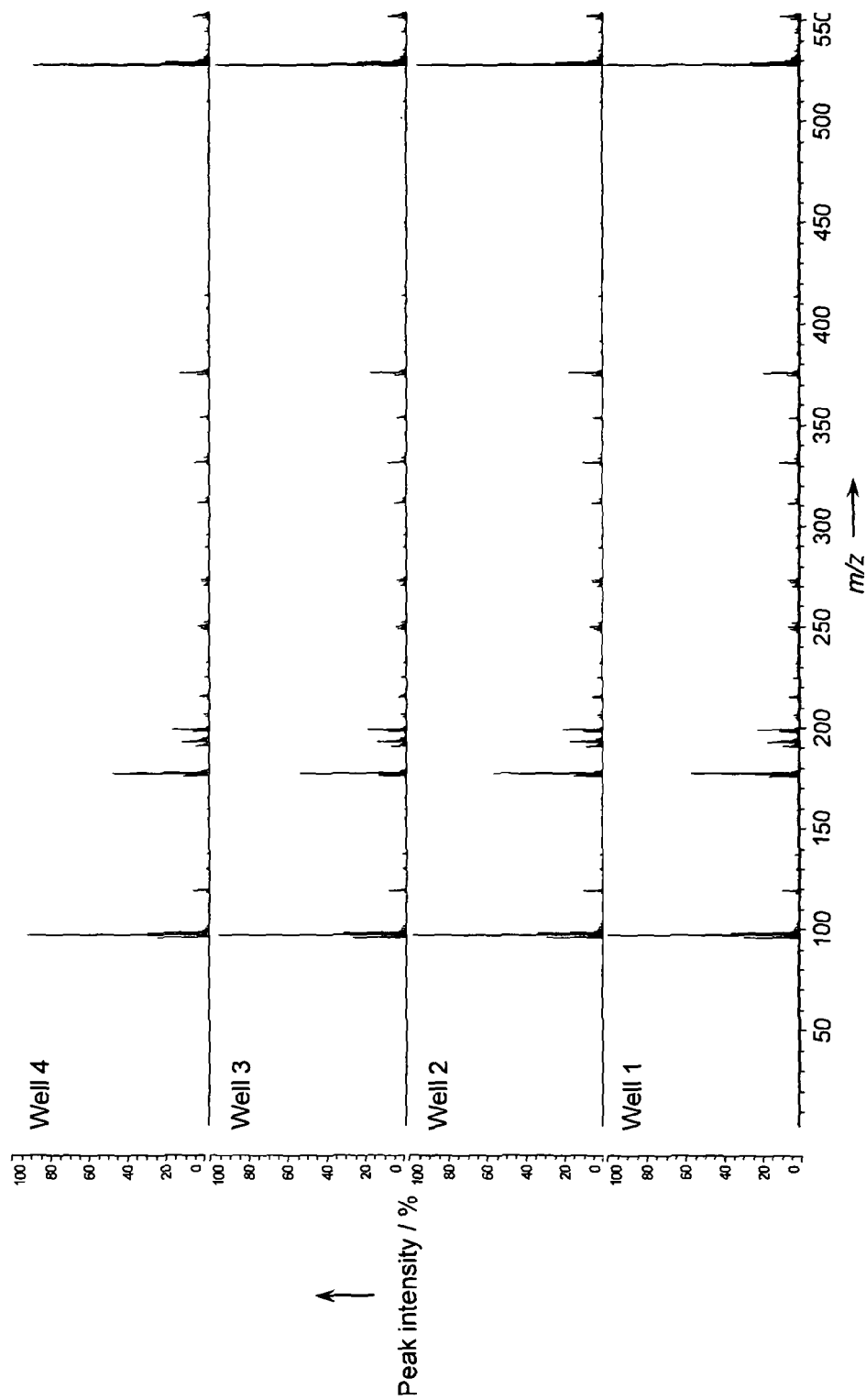
FIG. 3 shows the mass spectra of raffinose from four sample cavities normalized to the peak intensity in the spectrum of well 1.

The spectra of raffinose are shown in FIG. 3, the spectra were normalized to the peak intensity in the spectrum of well 1. The data shown in Table 1 demonstrate the good mass resolution and the outstanding reproducibility (low variation coefficient) of the peak intensity and the signal-to-noise-ratio (S/N). This demonstrates the outstanding reproducibility of results obtained by the present invention for a model system over results obtained for model systems by solvent-free methods of the prior art.

TABLE 1

Evaluation of the spectrum comparison of FIG. 3

|  | Peak intensity | S/N ratio | m/z |
|---|---|---|---|
| Mean | 325170 | 1114 | 527.18 |
| Standard deviation | 13519 | 45 | 0.015 |
| Variation Coefficient | 0.04 | 0.04 | 2.8 × 10−5 (28 ppm) |

Figure 4A:
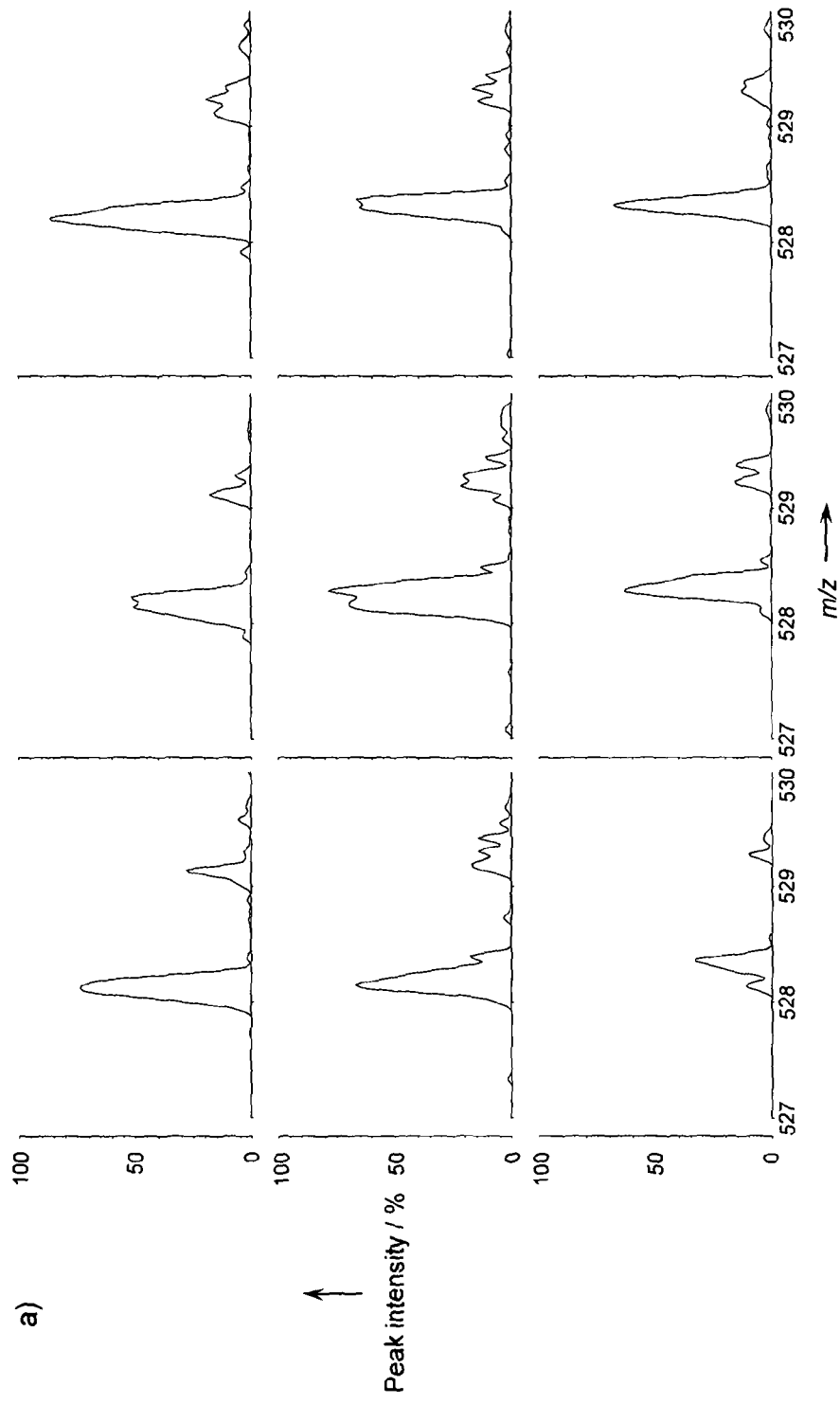
FIG. 4a shows shot-to-shot yield of the first 9 laser positions (2 laser shots per position) of raffinose.

The good reproducibility is the result of the comparable laser shot-to-shot yield (shown in FIG. 4a), which is based on the homogeneous distribution of the matrix/sample mixture, the substantially flat MALDI sample surface and the defined distance between the MALDI sample surface and the detector.

Example 2

Figure 4B:
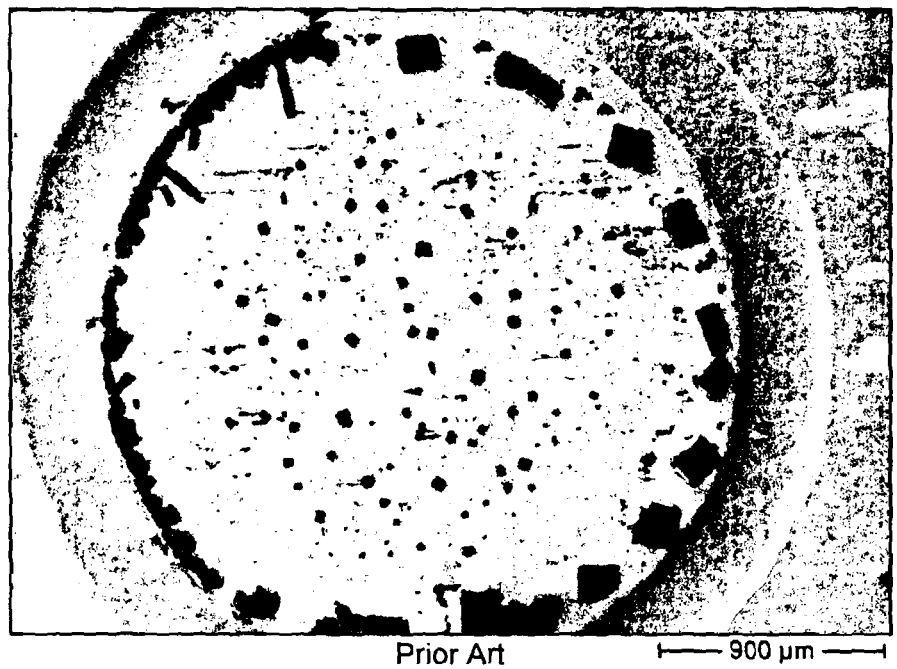
FIG. 4b shows a scanning electron microscope (SEM) picture of the sample surface obtained using the dried droplet (DD) technique of the prior art.
Figure 4C:
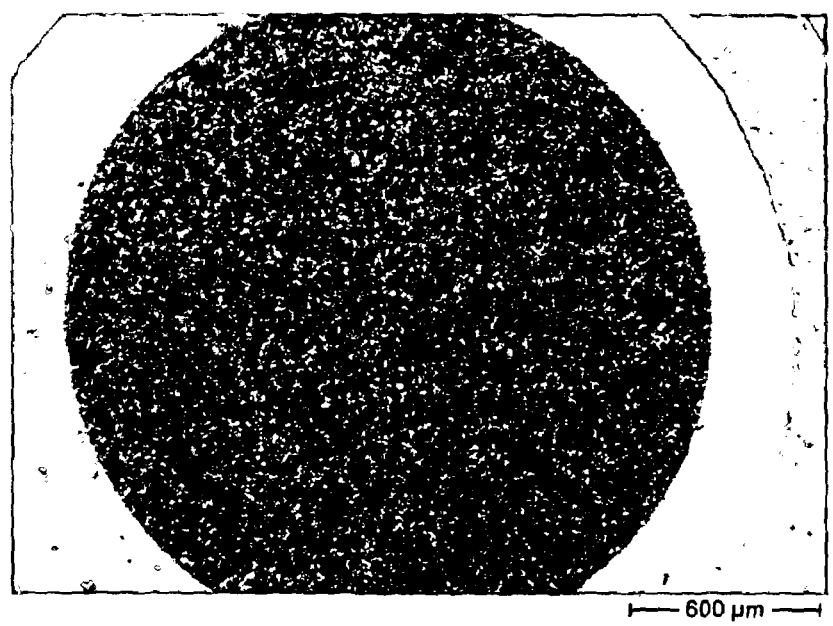
FIG. 4c shows a scanning electron microscope (SEM) picture of the MALDI sample surface obtained by the present invention.
Figure 4D:
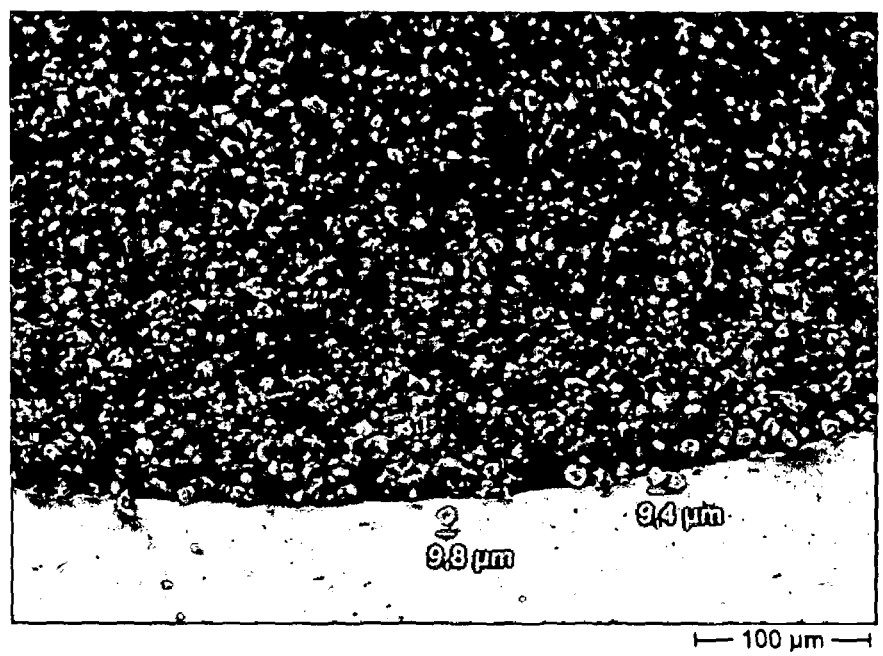
FIG. 4d shows a scanning electron microscope (SEM) picture of the MALDI sample surface obtained by the present invention.

The SEM picture shown in FIG. 4b shows the inhomogeneous distribution achieved with the classic DD technique of the prior art. FIGS. 4c and 4d are SEM pictures showing the outstanding homogeneous distribution of the matrix/sample mixture achieved with the compressed-sample (CS) technique of the present invention.

Example 3

Figure 5:
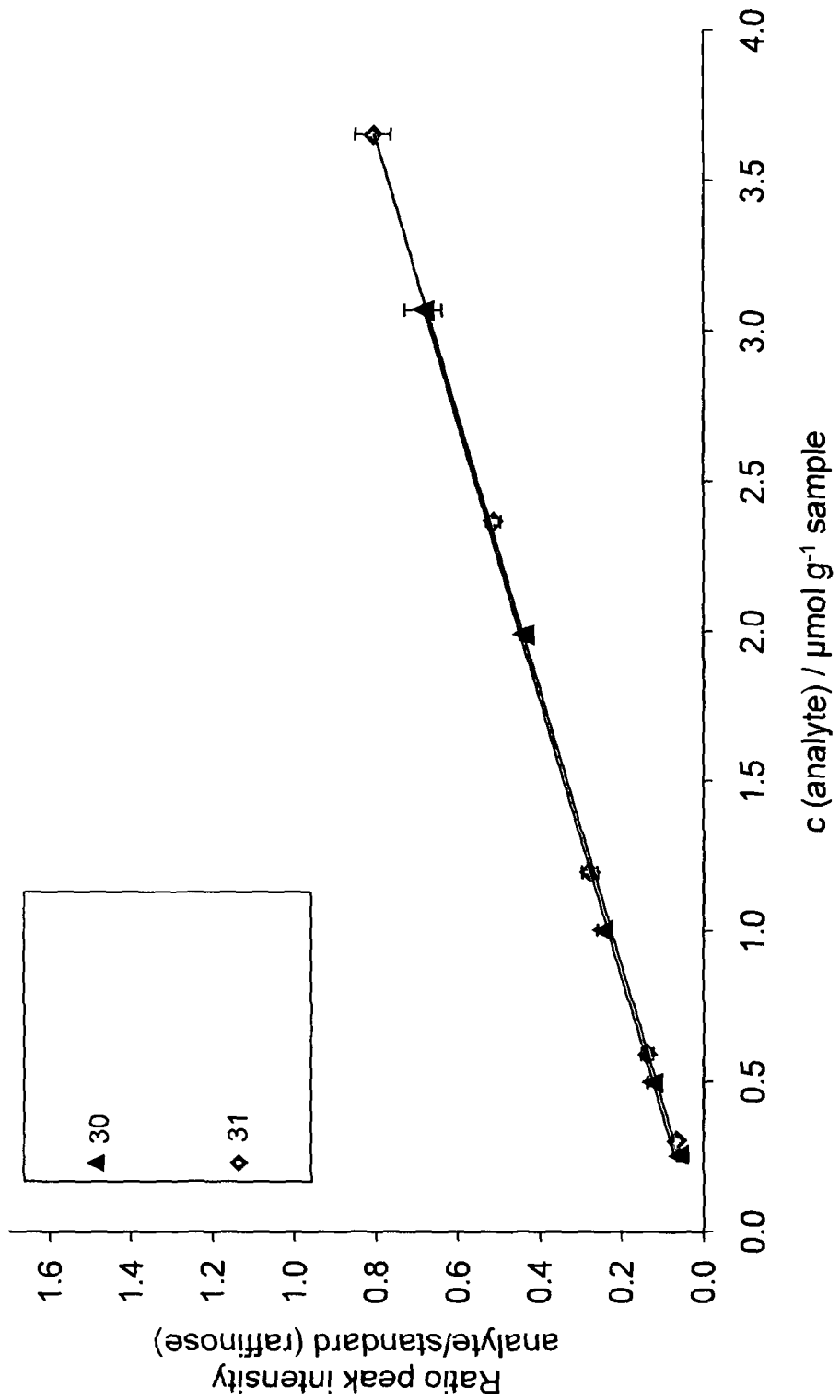
FIG. 5 shows the graphical plot of the calibration curves with raffinose as internal standard, and n-nonyl-β-D-maltoside (30) and n-undecyl-β-D-maltoside (31) as analytes.

FIG. 5 shows the graphical plot of the calibration curves (n=4) with raffinose as internal standard and n-nonyl-β-D-maltoside (30), and n-undecyl-β-D-maltoside (31), as analytes. 5 µL of a methanolic raffinose solution (2.6 mg/mL), which includes different concentrations of n-nonyl-β-D-maltoside (30) and n-undecyl-β-D-maltoside (31), was added to about 20 mg of the premix described in Example 1. The premix with the sample was mixed and homogenized in a mortar with a pestle.

The calibration curves shown in FIG. 5 are almost the same and show a correlation coefficient of 0.999. This demonstrates the effectiveness of quantitative analysis of results obtained by MALDI mass spectrometry according to the third aspect of the invention.

Example 4

To demonstrate that the CS technique of the present invention is also useful for real samples, a polydisperse alkylpolyglucoside (AG) with a chain length of $C_{12}$ or $C_{14}$ and a polymerization degree between 1 and 10 provided by Cognis GmbH was investigated by the CS technique as well as the DD method of the prior art. To verify the reproducibility of the sample preparation for the CS technique, four samples were prepared, and each was analyzed four times, while for the DD technique eight analyses were performed. The analyte (AG) was mixed with n-nonyl-β-D-maltoside as internal standard and with raffinose for a comparison. Table 2 shows the calculated ratios of the peak intensities, its mean values (MW) and the resulting variation coefficients (V).

TABLE 2

Ratio of the peak intensities of the shown compounds to the standard n-nonyl-β-D-maltoside with resulting variation coefficient analyzed by the CS and the DD technique

|  | Sample 1 n = 4 | Sample 2 n = 4 | Sample 3 n = 4 | Sample 4 n = 4 | $MW_{CS}$ | $V_{CS}$ | $MW_{DD}$ n = 8 | $V_{DD}$ |
|---|---|---|---|---|---|---|---|---|
| Raffinose | 1.20 ± 0.11 | 1.18 ± 0.11 | 1.08 ± 0.07 | 1.11 ± 0.07 | 1.14 ± 0.09 | 0.079 | 0.48 ± 0.19 | 0.396 |
| n-Undecyl-β-D-maltoside | 1.11 ± 0.15 | 1.05 ± 0.07 | 1.04 ± 0.03 | 1.03 ± 0.03 | 1.06 ± 0.08 | 0.075 | 0.96 ± 6.10 | 0.104 |
| $C_{12}$-Glucoside | 3.69 ± 0.44 | 3.95 ± 0.19 | 4.66 ± 0.40 | 4.42 ± 0.29 | 4.18 ± 0.34 | 0.081 | 3.68 ± 0.89 | 0.242 |
| $C_{14}$-Glucoside | 1.30 ± 0.11 | 1.32 ± 0.16 | 1.53 ± 0.10 | 1.40 ± 0.05 | 1.39 ± 0.10 | 0.072 | 1.25 ± 0.36 | 0.288 |
| $C_{12}$-Maltoside | 1.80 ± 0.11 | 1.61 ± 0.13 | 1.93 ± 0.07 | 1.70 ± 0.02 | 1.76 ± 0.09 | 0.051 | 1.14 ± 0.11 | 0.096 |
| $C_{14}$-Maltoside | 0.61 ± 0.04 | 0.56 ± 0.03 | 0.67 ± 0.09 | 0.56 ± 0.02 | 0.60 ± 0.05 | 0.083 | 0.43 ± 0.07 | 0.163 |

The results obtained allow, for example, the important determination of the $C_{14}$-glucoside/$C_{12}$-glucoside ratio of the AG used as 0.33 (CS technique) and 0.34 (DD technique). To validate these results, the analyses were also carried out with GC (0.33) and HPLC (0.32). Although in this case the DD technique yielded good results, the variation coefficients reveal much greater uncertainty in the results, while the CS technique yielded good precision (variation coefficient for all analytes ≤0.083). The difference in precision is particularly strong for analytes like raffinose, which differ significantly from the internal standard (0.079 versus 0.396).

After the successful use of the CS technique for real samples of synthetic organic polymers, it was of interest to investigate to what extent this method can be applied in the life-science sector and whether peptides with different sizes can be quantified with a single standard.

Example 5

Figure 6:
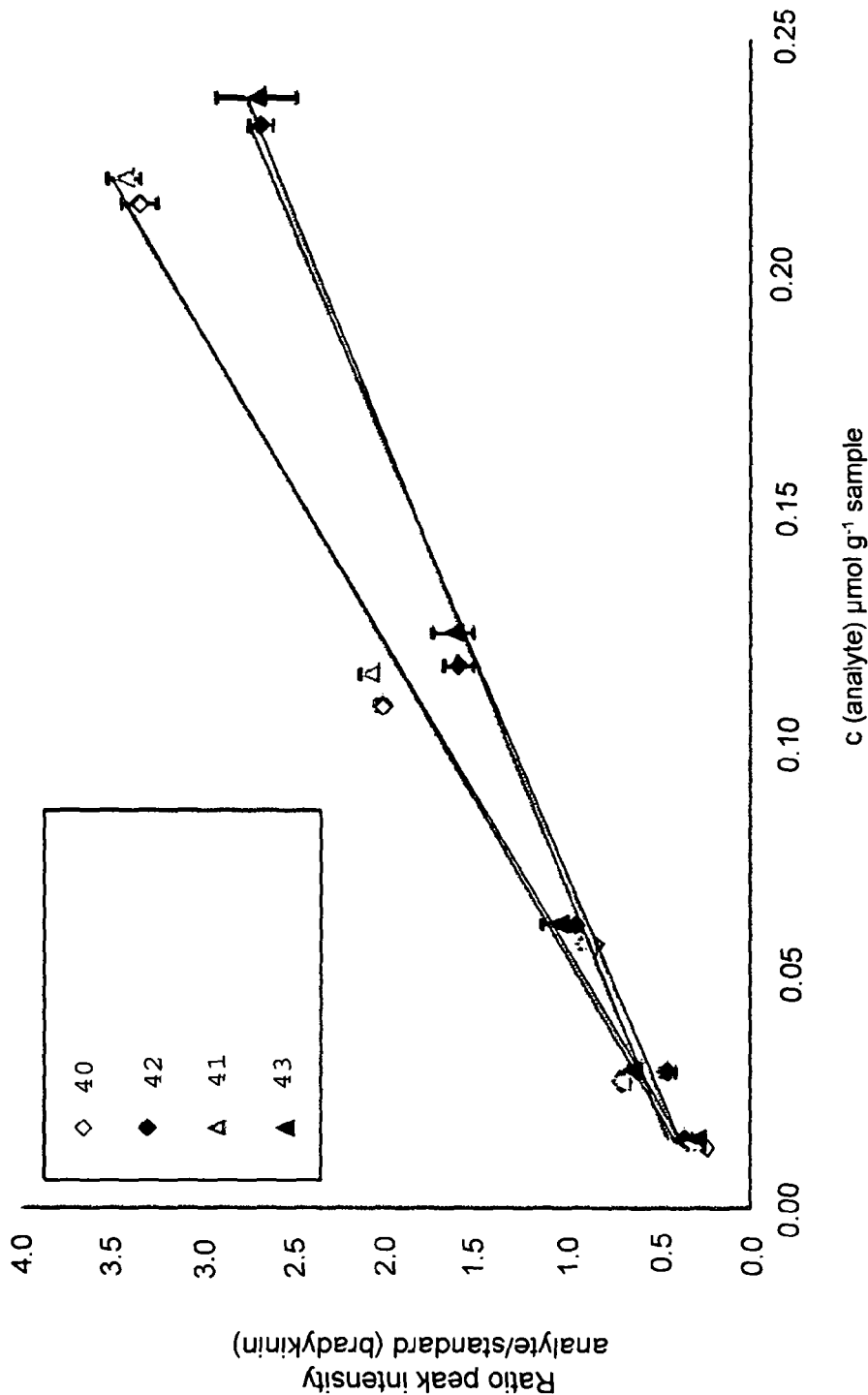
FIG. 6 shows the graphical plot of the calibration curves of bacitracin (40, 41) and gramicidin (42, 43) on different days with bradykinin as internal standard and sinapic acid as matrix.

FIG. 6 shows the calibration curves of bacitracin (40, 41) with 1423 Da and gramicidin (42, 43) with 1882 Da on two consecutive days (40 and 41, and 42 and 43) with freshly prepared samples and bradykinin (1060 Da) as internal standard and sinapic acid as matrix. The peptides were dissolved in methanol/0.5% TFA (w/w, 3:1). The bradykinin concentration was 0.06 mg/mL. A round laser raster with 241 profiles and 2 laser shots per profile was used.

The calibration curves of the two peptides are almost identical, which proves the suitability of the method for the quantitative determination of peptides. The simultaneous quantitative analysis of variously sized peptides is possible, whereby the application of MALDI in the life-science sector significantly increases. The slopes of the two peptides are probably not comparable because of different desorption and ionization yields, but can be corrected with the internal standard.

The CS technique presented allows the quantitative analysis of synthetic polymers and peptides with a hitherto unknown accuracy for MALDI without the use of stabile-isotope-labeled standards. This will greatly broaden the range of application of MALDI in the life-science sector, as well as in product and process analysis.

REFERENCES

A number of publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

[1] F. Hillenkamp, J. Peter-Katalinic, *MALDI MS—A Practical Guide to Instrumentation, Methods and Applications*, Wiley-VCH Verlag GmbH & Co. KGaA, Weinheim, 2007.
[2] S. M. Weidner, J. Falkenhagen, *Rapid Commun. Mass Spectrom.* 2009, 23, 653-660.
[3] N. Amini, M. Shariatgorji, G. Thorsen, *J. Am. Soc. Mass Spectrom.* 2009, 20, 1207-1213.
[4] E. Szajli, T. Feher, K. F. Medzihradszky, *Mol. Cell. Proteomics* 2008, 7, 2410-2418.
[5] M. Bucknall, K. Y. C. Fung, M. W. Duncan, *J. Am. Soc. Mass Spectrom.* 2002, 13, 1015-1027.
[6] W. Y. Yan, J. A. Gardella, T. D. Wood, *J. Am. Soc. Mass Spectrom.* 2002, 13, 914-920.
[7] A. Cristadoro, H. J. Rader, K. Mullen, *Rapid Commun. Mass Spectrom.* 2008, 22, 2463-2470.
[8] S. Trimpin, A. Rouhanipour, R. Az, H. J. Rader, K. Mullen, Rapid Commun. Mass Spectrom. 2001, 15, 1364-1373.
[9] L. Przybilla, J-D. Brand, K. Yoshimura, H. J. Rader, K. Mullen, Anal. Chem. 2000, 72, 4591-4597.
[10] S. Trimpin, S. Keune, R. Az, H. J. Rader, K. Mullen, J. Am. Soc. Mass Spectrom. 2006, 17, 661-671.

The invention claimed is:

1. A method of preparing a MALDI sample, the method comprising the steps of:
   (a) mixing a solid sample precursor comprising sample and MALDI matrix to form a solid sample mixture;
   (b) applying the solid sample mixture to a sample cavity of a MALDI target; and
   (c) compressing the solid sample mixture in the sample cavity so as to form a MALDI sample surface for laser desorption and ionisation;
   wherein the MALDI sample surface is formed by compressing the solid sample mixture against a surface forming means in order to provide a flat and homogeneous surface.

2. The method according to claim 1, wherein the sample surface formed is substantially level with the front surface of the MALDI target.

3. The method according to claim 1, wherein the MALDI sample surface formed has a height variation of less than 15 μm.

4. The method according to claim 1, wherein in the mixing step first the matrix components are pre-mixed, then the sample is added before mixing to form the solid sample mixture.

5. The method according to claim 1, wherein the sample comprises an analyte and the analyte is a polymer, a peptide or a protein.

6. The method according to claim 1, wherein the solid sample precursor includes a standard.

7. A MALDI target comprising a sample cavity for receiving a MALDI sample, the sample cavity having
   (a) a desorption end portion comprising an aperture, such that a portion of the MALDI sample exposed at the aperture is in use subjected to laser desorption and ionisation;
   and wherein the sample cavity also has
   (b) a compression end portion adapted to permit compression of a solid sample mixture towards the desorption end portion in the sample cavity by applying a compression force to the solid sample mixture via the compression end portion in order to provide a flat and homogeneous MALDI sample surface.

8. The MALDI target according to claim 7, wherein the compression end portion comprises an aperture for receiving a compression means.

9. The MALDI target according to claim 7, wherein the sample cavity is a through hole.

10. A method of quantitative analysis of a sample, the method comprising the steps of:
    (a) preparing a MALDI sample according to claim 6;
    (b) analysis of the MALDI sample in a MALDI mass spectrometer; and
    (c) quantitative analysis of the results obtained by mass spectrometry with reference to the standard.

11. A method of quantitative analysis of a sample, the method comprising the steps of:
    (a) mixing a solid sample precursor comprising sample, MALDI matrix and a standard to form a solid sample mixture;
    (b) applying the solid sample mixture to a sample cavity of the MALDI target of claim 7;
    (c) compressing the solid sample in the sample cavity so as to form a MALDI sample surface for laser desorption and ionisation;
    (d) analysis of the MALDI sample surface in a MALDI mass spectrometer;
    (e) quantitative analysis of the results obtained by mass spectrometry with reference to the standard.

12. A method according to claim 10, wherein the mass spectrometer is a TOF MS.

13. A method according to claim 10, wherein the solid sample precursor comprises a single standard and a plurality of chemically related analytes.

14. A MALDI target comprising a plurality of sample cavities, each sample cavity for receiving a MALDI sample, each sample cavity having
   (a) a desorption end portion comprising an aperture, such that a portion of the MALDI sample exposed at the aperture is in use subjected to laser desorption and ionisation;
   and wherein each sample cavity also has
   (b) a compression end portion adapted to permit compression of a solid sample mixture towards the desorption end portion in the sample cavity by applying a compression force to the solid sample mixture via the compression end portion in order to provide a flat and homogeneous MALDI sample surface.

* * * * *